United States Patent [19]

Takafuji et al.

[11] Patent Number: 4,719,583

[45] Date of Patent: Jan. 12, 1988

[54] METHOD AND APPARATUS OF EVALUATING MECHANICAL PROPERTIES OF STEEL

[75] Inventors: Hideo Takafuji; Tsugio Ishida; Shoichi Sekiguchi, all of Kawasaki, Japan

[73] Assignee: Nippon Steel Corporation, Tokyo, Japan

[21] Appl. No.: 662,976

[22] Filed: Oct. 18, 1984

[30] Foreign Application Priority Data

Oct. 21, 1984 [JP] Japan ............................. 58-197255

[51] Int. Cl.$^4$ ..................... G06G 7/68; G06F 15/20; G01N 3/00; G01N 3/08
[52] U.S. Cl. ................................... 364/506; 364/507; 364/551; 364/552; 73/78; 73/760; 73/826
[58] Field of Search ............... 364/506, 507, 508, 552, 364/550, 551; 73/760, 78, 594, 826, 19

[56] References Cited

U.S. PATENT DOCUMENTS

| | | | |
|---|---|---|---|
| 3,003,351 | 10/1961 | Ziegler et al. | 73/597 |
| 3,003,352 | 10/1961 | Ziegler et al. | 73/597 |
| 3,905,222 | 9/1975 | Boillot | 73/19 |
| 4,080,836 | 3/1978 | Thompson et al. | 73/760 |
| 4,133,722 | 1/1979 | Ensanian | 73/763 |
| 4,320,463 | 3/1982 | Hummelstein | 364/552 |
| 4,335,352 | 6/1982 | Stephen | 324/228 |
| 4,481,470 | 11/1984 | Wallace | 324/228 |
| 4,495,587 | 1/1985 | Plante et al. | 364/552 |
| 4,530,235 | 7/1985 | Shabel | 73/81 |
| 4,567,774 | 2/1986 | Manahan et al. | 73/826 |

OTHER PUBLICATIONS

"An Investigation of the Precipitation-Hardening Process in Aluminum Alloy 2219 by Means of Sound Wave Velocity and Ultrasonic Attenuation", Rosen et al. *Material Science and Engineering*, 53 (No. 2) May 1982, pp. 163-177.
Dieter, Mechanical Metallurgy (2nd Edition), McGraw-Hill Book Co., 1976, pp. 227, 268, 284, 355 and 373.
George et al., Metal Progress, *Estimating Yield Strength from Hardness Data*, American Society for Metals, vol. 109, No. 5, May 1976, pp. 30-34.
Bowden et al., *The Friction and Lubrication of Solids*, Oxford University Press, 1950, pp. 10-30.

*Primary Examiner*—Parshotam S. Lall
*Assistant Examiner*—Danielle Laibowitz
*Attorney, Agent, or Firm*—Wenderoth, Lind & Ponack

[57] ABSTRACT

In order to evaluate the mechanical properties of steel, empirical equations showing the relationship between each of the tensile strength, yield point and elongation of steel and its hardness, grain size and chemical composition are determined in advance based on experimental results. Then, the hardness, grain size and chemical composition of the steel to be evaluated are determined. The tensile strength, yield point and elongation of the steel to be evaluated are determined by inserting the determined hardness, grain size and chemical composition in the empirical equations. In determining the energy absorbed according to a method of this invention, empirical equations showing the relationship between each of the shelf energy, transition temperature and temperature range of the energy transition region of steel and its hardness, grain size and chemical composition are determined in advance. Then, the hardness, grain size and chemical composition of the steel to be evaluated are determined. The shelf energy, transition temperature and temperature range of the energy transition region of the steel to be evaluated are then derived by inserting the determined hardness, grain size and chemical composition in the empirical equations. Finally, the energy absorbed at a given temperature is derived from the shelf energy, transition temperature and temperature range of the energy transition region thus determined.

8 Claims, 9 Drawing Figures

METHOD AND APPARATUS OF EVALUATING MECHANICAL PROPERTIES OF STEEL

BACKGROUND OF THE INVENTION

1. Field of the Invention

This invention relates to a method and apparatus of evaluating the mechanical properties of steel.

2. Description of the Prior Art

Of various properties of steel, mechanical properties such as strength and toughness are the most important. The tensile test is a test commonly conducted for the determination of steel strength. As is well-known, standard tension specimens are taken and prepared from a portion of the steel to be tested in accordance with such standards as ASTM and JIS. The specimens thus prepared are subjected to tensile and breaking loads using a tension testing machine under given conditions. Measures expressing the strength of steel to withstand deformation and fracture, such as tensile strength, yield point and elongation, are derived from the stress-strain curve and the shape and dimensions of the broken specimen established through the test.

The Charpy test is a test widely used to determine the toughness of steel. In the Charpy test, a specimen prepared to a standard is kept at a given temperature (commonly a low temperature below room temperature) and broken on a Charpy testing machine. The energy absorbed and the percent shear appearance of the fracture surface are determined.

In a steelmaking process, for instance, an inspection line is provided at the farthest end of its process line. A test specimen is taken from a portion of product, prepared as required, and put to mechanical tests to determine and guarantee the mechanical properties of the steel product being tested. Sampling and preparation of test specimens and implementation of mechanical tests require much time and money.

SUMMARY OF THE INVENTION

This invention has been made to dispense with the aforementioned shortcomings with conventional testing methods and apparatuses. An object of this invention is to provide an easy, rapid and economical method of evaluating the mechanical properties of steel products.

Another object of this invention is to provide a method of evaluating mechanical properties with an accuracy analogous to that of conventional methods that can be used as a substitute therefor.

Still another object of this invention is to provide an apparatus that can be incorporated in a manufacturing process for automatic evaluation of the mechanical properties of steel products and judgement of the acceptability thereof.

In order to achieve the aforementioned objects, a method of evaluating the mechanical properties of steel products according to this invention includes deriving empirical equations showing the relationships between each of the tensile strength, yield point and elongation and the hardness, grain size and chemical composition of first steel samples on the basis of experimental data. Then, the hardness, grain size and chemical composition of at least one second steel sample to be evaluated are determined. By using the empirical equations and the values thus determined, the tensile strength, yield point and elongation of the second steel sample in question are determined.

In determining the energy absorbed according to a mechanical properties evaluating method of this invention, empirical equations showing the relationships between each of the shelf energy, transition temperature, and temperature range in the energy transition zone and the hardness, grain size and chemical composition of first steel samples are previously determined. Then, hardness, grain size and chemical composition of at least one steel sample to be evaluated are determined. By using the empirical equations and the values thus determined, the shelf energy, transition temperature and temperature range in the energy transition zone of the second steel sample in question are determined. The energy absorbed at a given temperature is then derived from the shelf energy, transition temperature and temperature range in the energy transition zone.

An apparatus for evaluating the mechanical properties of steel according to this invention comprises a hardness measuring apparatus, a grain size measuring apparatus, a chemical composition analyzing apparatus and a computer positioned at the terminal end of a production line. The computer comprises an input unit to bring the measured data into the computer, a memory, an arithmetic logic unit, and a display. Signals outputted from the hardness and grain size measuring apparatuses and emission spectrochemical analyzer are taken into the computer through the input unit. The memory stores the empirical equations expressing the relationship between each of the tensile strength, yield point, elongation, shelf energy, transition temperature and temperature range of the energy transition zone and the hardness, grain size and chemical composition of steel and the energy transition curves plotting the shelf energy, transition temperature and temperature range of the energy transition zone as their parameters. The arithmetic logic unit derives the energy absorbed at a given temperature from the tensile strength, yield point, elongation, shelf energy, transition temperature, temperature range of the energy transition zone and energy transition curves by inserting the data from the measuring instruments in the equations stored in the memory. The display shows the results of arithmetic operation outputted from the arithmetic logic unit.

In the conventional mechanical testing methods widely used, sampling and preparation of test specimens have been so time-consuming that it often takes several days before the results of a test is obtained. With the method of this invention, by contrast, it is possible to know the results within a few hours since the machining of test specimens is dispensed with. It is also possible to conduct an on-line test according to this invention. Furthermore, the products rejected by the test according to this invention may be re-tested by a conventional method for reassurance. Therefore, the testing method and apparatus of this invention permits evaluating the mechanical properties of steel in a highly simplified manner and in a drastically shortened time. The testing process that has conventionally been time-consuming and costly can now be streamlined in great measure.

DESCRIPTION OF THE PREFERRED EMBODIMENTS

First, a method of evaluating mechanical properties of steel from the measures of hardness, grain size and chemical composition, unlike the conventional tensile and impact tests, which constitutes the essential point of this invention will be described.

Hardness testing is widely used as a simple means of determining mechanical strength of steel. Brinnel, Rockwell and Vickers hardness tests are well-known. It is said that the hardness determined by these methods corresponds to tensile strength, although there are some variations with different testing and display methods.

Grain size is one of the most fundamental and important factors that govern the mechanical properties of steel. Grain refining enhances both strength and toughness. For the evaluation of grain size, a test specimen is usually machined and ground, with the grain boundaries exposed by applying surface etching. The estimation of grain size is made by visually examining the exposed surface under a microscope. The term "grain size" usually means the ferrite or original austenite grain size. In this invention, however, effective grain size that practically governs the mechanical properties of steel is used. The effective grain size is the size of grains bounded by boundaries where crystal orientation changes greatly. The ferrite grain size for ferritic-pearlitic steels and the covariant packet size for martensitic and bainitic steels are examples of the effective grain size.

Chemical composition is determined by a common method using, for example, an emission spectroscopic analyzer.

Figure 1:
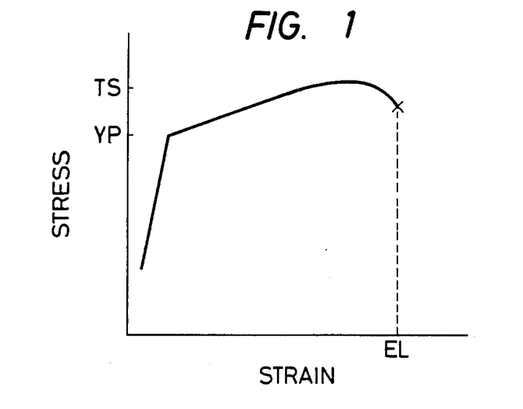
FIG. 1 is a stress-strain curve of steel subjected to the tensile test.

Now a method of this invention for estimating the mechanical properties of steel using the hardness, grain size and chemical composition that are determined as described above will be discussed. FIG. 1 shows a stress-strain curve derived from a tensile test. The information derived from the tensile test are generally tensile strength TS, yield point YP and elongation EL.

The evaluation of tensile strength TS is made principally on the basis of hardness H. As mentioned previously, there is a strong correlation between hardness H and tensile strength TS. However, hardness H and tensile strength TS do not agree with each other very closely as the deformation mode in the tensile test differs from that in the indentation hardness test. Influenced by the work hardening properties, the relationship between hardness H and tensile strength TS is usually expressed as follows:

$$TS = f_1(H, n) \tag{1}$$

where n is a work-hardening exponent. Work hardening is a property of steel that depends upon the grain size and structure thereof. The structure is generally determined by the chemical composition of each steel and the conditions of working and heat treatment to which the steel is subjected. But where the manufacturing process is stable, the structure is determined almost solely by the chemical composition.

As such, the evaluation according to this invention is centered on hardness H as shown in the following equation, with grain size Du and chemical composition $(X_j)$ where $j=1$ to N used as supplementary parameters:

$$TS = f_1(H, Du, (X_j)) \tag{2}$$

$$= f_{11}(H) + f_{12}(Du,(X_j)) \tag{3}$$

Here, the term $f_{12}$ makes less of a contribution than the term $f_{11}$.

For practical purposes, the following linear equation is used.

$$TS = \alpha_1[H] + \alpha_2[Du^{-\frac{1}{2}}] + \alpha_3[C] + \alpha_4[Mn] \tag{4}$$

where $\alpha_i$ is an experimentally determined constant, C is carbon content and Mn is manganese content. Hall-Petch's well-known equation $\sigma_y = k_0 + kd^{-\frac{1}{2}}$ expresses the relationship between the strength $\sigma_y$ and grain size d of steel. The method of this invention is also modeled on that equation.

Yield point YP exhibiting the deformation strength of steel without work hardening is one of the most fundamental mechanical properties. Tensile strength TS is derived from yield point YP taking into account the work hardening characteristic of steel. According to the method of this invention, therefore, yield point YP is estimated by subtracting the increment due to work hardening from the estimated value of tensile strength TS.

$$YP = f_2(H, Du, (X_j)) \tag{5}$$

$$= f_1(H, Du, (X_j)) - f_{21}(Du, (X_j)) \tag{6}$$

The contribution of the term $f_{21}$ is due to the mechanical properties of steel and is generally larger than that of the term $f_{12}$ in equation (3).

For practical purposes, the following equation is used:

$$YP = \beta_1[H] + \beta_2[Du^{-\frac{1}{2}}] + \beta_3[C] + \beta_4[Mn] \tag{7}$$

where $\beta_i$ is a constant.

Elongation EL varies with the properties of steel, especially with tensile strength TS. Since elongation varies also with the shape and dimensions of a test specimen, the following equation is used for estimation:

$$EL = f_3(H, Du, A, L, (X_j)) \tag{8}$$

For practical purposes, the following equation is used:

$$EL = \gamma_1[H] + \gamma_2[Du^{-\frac{1}{2}}] + \gamma_3[C] + \gamma_4[Mn] + \gamma_5[A^{\frac{1}{2}}] + \gamma_6[L] \tag{9}$$

where $\gamma_i$ is a constant, A and L respectively designate the cross-sectional area and length of the reduced section of the tension specimen to be evaluated.

Figure 2:
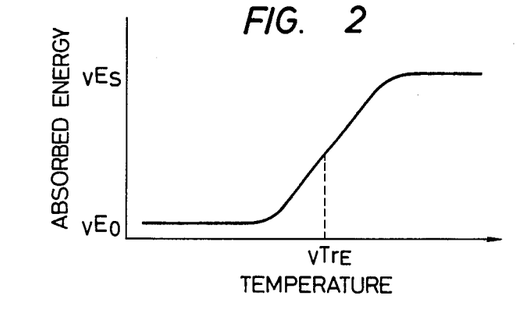
FIG. 2 is an absorbed energy transition curve of steel subjected to the Charpy test.

Now a method of estimating the impact resisting properties according to this invention will be described. FIG. 2 shows a transition curve resulting from the Charpy impact test, with the testing temperature T (°C.) plotted as abscissa and the absorbed energy vE (kg·m) as ordinate. In impact tests, the amount of energy absorbed vET at a given testing temperature is usually determined. In the method of this invention, therefore, the transition curve is expressed by the upper shelf energy vEs, lower shelf energy vEo ($\approx 0$) and energy transition temperature vTrE.

$$vET = g(vEs, vEo, vTrE, T) \tag{10}$$

Figure 3:
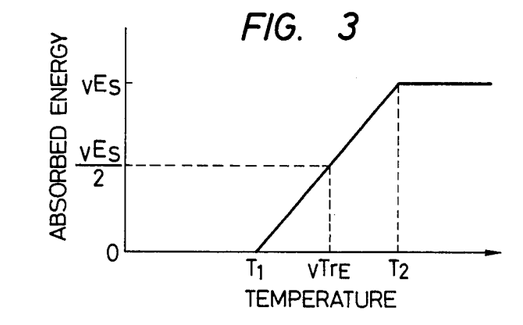
FIG. 3 is a simplified diagram similar to FIG. 2.

In FIG. 3, the transition region in FIG. 2 is linearly approximated. Equation (10) is then expressed as follows:

$$vE_T = \begin{cases} 0 & T \leq T_1 \\ vEs\left(\dfrac{T - vTrE}{T_2 - T_1} + \dfrac{1}{2}\right) & T_1 \leq T \leq T_2 \\ vEs & T_2 < T \end{cases} \tag{11}$$

In this equation, the lower shelf energy vEo is 0. The upper shelf energy vEs, energy transition temperature vTrE, and the range of the energy transition region $T_2 - T_1$ are expressed as follows using hardness H, grain size Du and chemical composition $(X_j)$, j being 1 to N:

$$vEs = h_1(H, Du, (X_j)) \tag{12}$$

$$vTrE = h_2(H, Du, (X_j)) \tag{13}$$

$$T_2 - T_1 = h_3(H, Du, (X_j)) \tag{14}$$

By using equations (12), (13) and (14), the energy absorbed vET at a given temperature T is derived from hardness H, grain size Du and chemical composition $(X_j)$.

The fracture transition temperature vTrs that is widely used as a characteristic determined by the Charpy test is also expressed by the following equation (15).

$$vTrs = h_4(H, Du, (X_j)) \tag{15}$$

For practical purposes, the following equations are used:

$$vEs = \delta_1[H] + \delta_2[Du^{-\frac{1}{2}}] + \delta_3[C] + \delta_4[Mn] \tag{16}$$

$$vTr = \epsilon_1[H] + \epsilon_2[Du^{-\frac{1}{2}}] + \epsilon_3[C] + \epsilon_4[Mn] \tag{17}$$

$$T_2 - T_1 = \xi_1[H] + \xi_2[Du^{-\frac{1}{2}}] + \xi_3[C] + \xi_4[Mn] \tag{18}$$

$$vTrs = \eta_1[H] + \eta_2[Du^{-\frac{1}{2}}] + \eta_3[C] + \eta_4[Mn] \tag{19}$$

where $\delta_i$, $\epsilon_i$, $\xi_i$ and $\eta_i$ are constants.

As described above, the method of this invention permits easy determination of various mechanical properties, which have conventionally been evaluated by tensile and impact tests, from hardness H, grain size Du and chemical composition $(X_j)$. The following paragraphs describe an example in which the method of this invention was applied on steel plate for general structural purposes.

Figure 4:
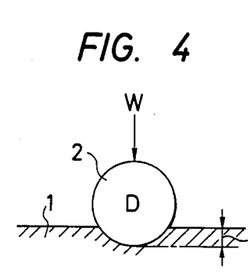
FIG. 4 is a schematic illustration of an indentation hardness testing method used in a preferred embodiment.
Figure 5:
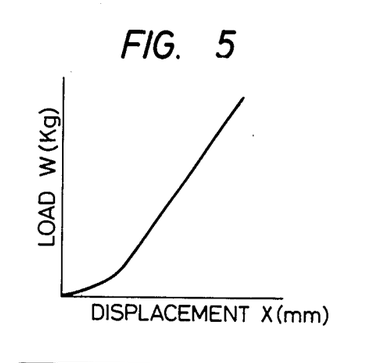
FIG. 5 shows an indentation load-displacement curve obtained by the testing method shown in FIG. 4.

FIG. 4 schematically illustrates the principle of the hardness measuring method used according to the present example With an indenter 2 having a diameter D (mm) pressed into a steel test specimen 1, the load W (kg) applied and the depth of indentation X (mm) were continuously measured. FIG. 5 shows a load-displacement curve thus determined. As may be seen, the load-displacement curve becomes a straight line when the load (or displacement) exceeds a certain point. By differentiating the value within such a range or determining the value of dW/dX, hardness HT is defined by the following equation:

$$H_T = k_1 \frac{1}{D} \frac{dW}{dX} \tag{20}$$

Usually, the hardness test is used as a simple substitute for the tensile test. The correspondence of the hardness defined by equation (20) to tensile strength TS is theoretically established as shown below. The Meyer hardness derived from the diameter d of the indentation produced is expressed as:

$$H_M = \frac{4W}{\pi d^2} \tag{21}$$

It is known that the Meyer hardness that results when the indenter is pressed into a perfect plastic deformation region of a material that does not work harden or that has fully work hardened exhibits the yield point YP or tensile strength TS of the material at that point.

$$H_M = k_2 \cdot Y = k_3 \cdot TS \tag{22}$$

where $k_1$, $k_2$ and $k_3$ are constants.

The following relationship holds among the depth X and diameter d of the indentation produced and the diameter D of the indenter used.

$$d = 2\sqrt{X(D - X)} \approx 2\sqrt{X \cdot D} \tag{23}$$

From equations (21), (22) and (23), accordingly, $$H_T = k_1 \cdot \frac{1}{D} \cdot \frac{dW}{dX} = k_1 \cdot \frac{1}{D} \cdot \frac{d}{dX}(\pi D \cdot k_3 \cdot TS \cdot X) \tag{24}$$
$$= k_4 \cdot TS$$

The above description is based on the assumption that the material being tested does not work harden. In actuality, however, the effect of work hardening must be somewhat taken into consideration. Even so, the hardness HT essentially corresponds to the tensile strength TS of steel. As mentioned previously, the hardness of steel is expressed in various ways such as the Brinell hardness. The differentiated hardness HT as defined by equation (20) has a theoretically established relationship with tensile strength TS and other mechanical properties as mentioned before. In this example, therefore, the differentiated hardness HT is used as hardness H in empirical equations (4), (7), (9) and (16) through (19).

Figure 6A:
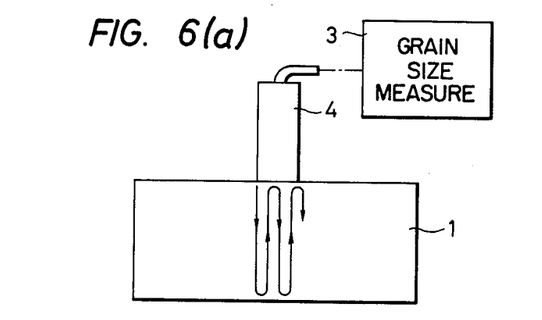
FIG. 6(a) is a schematic illustration of a method of determining the attenuation constant of ultrasonic waves used in a preferred embodiment.
Figure 6B:
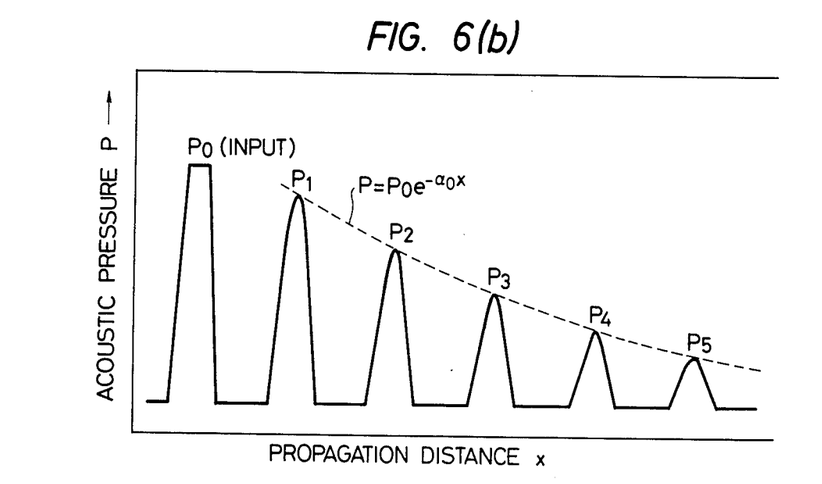
FIG. 6(b) is a graphical representation of the result obtained.

The grain size determining method employed in the example of application will be described in the following. FIG. 6(a) schematically illustrates an ultrasonic method of determining an attenuation constant. Ultrasonic waves are passed from a grain size measuring apparatus proper 3 through an ultrasonic wave oscillator 4, which serves as a transmitter-receiver, to a test specimen 1. The ultrasonic waves from the oscillator 4 are reflected multiply within the test specimen 1. From the series of acoustic pressure echoes detected by the oscillator 4, an attenuation curve as shown in FIG. 6(b) is obtained. Attenuating substantially exponentially with respect to the distance of propagation $\times$(cm), the acoustic pressure P of the echoes can be expressed as $P = P_0 e^{-\alpha x}$. If acoustic pressures at propagation distances $x_1$ and $x_2$ within the test specimen are $P_1$ and $P_2$, then the attenuation constant $\alpha$ (dB/cm) is defined by the following equation:

$$\alpha = \frac{20 \log (P_1/P_2)}{x_2 - x_1} \quad (25)$$

In actual measurement, the attenuation of ultrasonic waves results not only from the scattering at grain boundaries but also from the ultrasonic diffraction within the specimen, the reflection loss at both edges of the specimen, and some other causes. Since these causes are known ones, however, the attenuation induced thereby can be corrected. When the real attenuation constant $\alpha$ (dB/cm) is determined using an appropriate frequency f (Hz) as described above, grain size Du can be determined by inserting the values of $\alpha$ and f in an empirical equation as shown below.

$$Du = q(\alpha, f) \quad (26)$$

If the constant of elasticity is discontinuous between individual crystals, ultrasonic waves propagating through the test specimen are prevented from advancing further at grain boundaries and thereby caused to scatter and decay. Accordingly, the grain size determined by use of the attenuation of the energy of ultrasonic waves is what is known as the effective grain size characterized by the wide variations in crystallographic orientation between individual grains. With the steel plate as used in the example being described, the effective grain size corresponds to the ferrite grain size in the case of ferritic-pearlitic steels and the covariant packet size in the case of martensitic and bainitic steels. The effective grain size represents a crystal unit that practically governs the mechanical properties of steel to resist deformation, fracture and so on.

For chemical analysis, the values determined by a method known as the ladle analysis, in which samples are taken from the steel poured from the ladle used in the steelmaking process.

Tensile strength and other mechanical properties were determined by inserting the above data in the following equations that had been established in advance.

$TS = 0.0952(H) - 0.248(Du^{-\frac{1}{2}}) + 24.8(C) + 3.54(Mn) - 4.27$
$YP = 0.119(H) + 0.6979(Du^{-\frac{1}{2}}) - 31.1(C) - 3.95(Mn) - 21.0$ $EL = -0.0545(H) - 0.275(Du^{-\frac{1}{2}}) + 0.741(\sqrt{A}) -$
$\quad\quad\quad\quad\quad\quad\quad\quad\quad\quad 0.131(L) + 3.71(C) - 1.88(Mn) + 60.6$
$vEs = -0.044(H) - 0.164(Du^{-\frac{1}{2}}) - 118(C) - 9.7(Mn) + 60$
$vTr_E = -0.048(H) - 10.3(Du^{-\frac{1}{2}}) + 192(C) - 43(Mn) + 53$
$T_2 - T_1 = 0.157(H) - 7.38(Du^{-\frac{1}{2}}) + 47.8(C) + 15.4(Mn) + 14$ Chemical composition is expressed in percentage.

When compared with the values determined by conventional mechanical tests, the values evaluated by applying the methods of this invention just described to the steel plate agreed with high accuracy as shown below. By using many specimens having tensile strength of, for instance, 40 kg/mm$^2$ to 100 kg/mm$^2$, the range within which the method of this invention can be used for determining various levels of mechanical properties was ascertained.

|  | (A) | (B) |
| --- | --- | --- |
| Tensile strength TS (kg/mm$^2$) | 40–100 | 0.8 |
| Yield point YP (kg/mm$^2$) | 25–80 | 1.0 |
| Elongation EL (%) | 20–65 | 1.5 |
| Shelf energy vEs (kg.m) | 10–30 | 2.0 |
| Energy absorbed at −20° C. vE$_T$ (kg.m) | 2–30 | 2.2 |
| Energy transition temperature vTr$_E$ | −120—−20 | 7.6 |

*(A): The measurable range by the conventional testing methods.
(B): The accuracy with which the results obtained by the method of this invention agree with those obtained by the conventional methods.

The measurable range by the conventional testing methods indicates the range within which the results of the conventional tests conducted on the large number of specimens mentioned previously fall. Meanwhile, the accuracy of agreement is the mean square of the difference between the results of measurement obtained by the conventional methods and the results of arithmetic operation according to the method of this invention.

Figure 7:
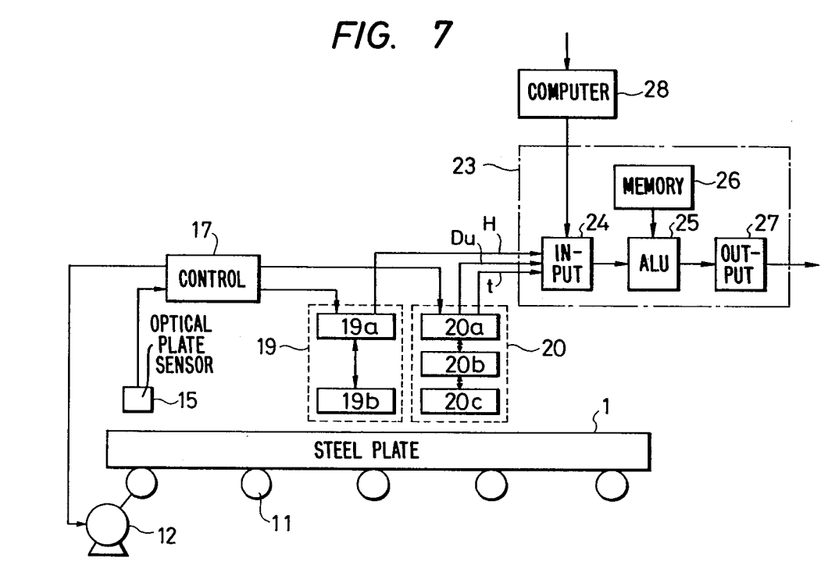
FIG. 7 shows the construction of an apparatus used for the implementation of a testing method according to this invention.
Figure 8:
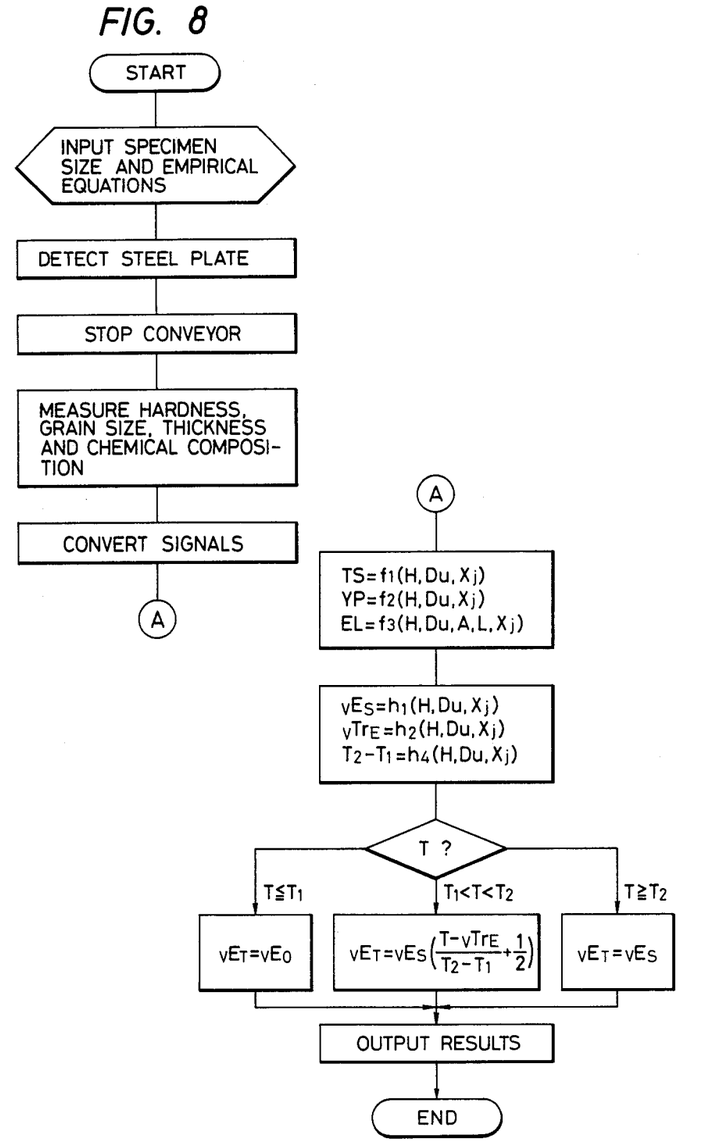
FIG. 8 is a flowchart showing the sequence of operations in the evaluation of the mechanical properties of steel using the apparatus shown in FIG. 7.

The following paragraphs describe an apparatus that is used in implementing the method of this invention just described in a steel plate production line. FIG. 7 shows an apparatus according to this invention that is incorporated in a production line. FIG. 8 is a flowchart showing a process in which mechanical properties of steel are determined using the apparatus shown in FIG. 7.

As illustrated, an optical plate sensor 15 inputs a detection signal to a control unit 17 as a steel plate 1 is carried into an inspection line by a conveyor 11. On receiving a signal from the control unit 17, the motor 12 of the conveyor 11 stops to hold the plate 1 in an inspecting position.

Then, a signal from the control unit 17 is inputted in the control operation section 19a of a hardness measuring apparatus 19. The control operation section 19a lowers the measuring head 19b thereof onto the plate to cause a steel ball at the tip thereof to be pressed in the surface of the steel plate. The control operation section 19a derives the hardness of the plate from the indentation load-displacement curve and inputs the obtained data into a computer 23.

A signal from the control unit 17 is also inputted in a grain size measuring apparatus 20 which comprises a measuring head 20c, ultrasonic-wave transmitter-receiver 20b, and a control operation section 20a. To the measuring head 20c is attached an ultrasonic wave oscillator and a contact catalyst ejecting mechanism. On receiving a signal from the control unit 17, the control operation section 20a lowers the measuring head 20c onto the plate and determines the attenuation of ultrasonic waves using the oscillator that is held in contact with the steel plate 1 via the contact catalyst. On the basis of the attenuation signal thus obtained, the control operation section 20a calculates the grain size and inputs the obtained data into the computer 23.

The chemical composition determined by the ladle analysis is inputted in advance in a line operation control computer 28 and is used for the arithmetic operation carried out in the computer 23.

The results of each measurement are inputted in an input section 24 of the computer 23 where analog signals are converted to digital signals. Using the signals from the input section 24 and the empirical equations and transition temperature curve stored in a memory 26, an arithmetic logic unit 25 calculates the tensile strength, yield point, elongation and energy absorbed at a given temperature. The results obtained are outputted through an output section 27 to a heat treatment apparatus, display unit or the like (not shown). The computer used here is of the general-purpose type, such as the IBM HP-9836.

Provision may be made so that the results obtained can be compared in the arithmetic logic unit 25 with the target values stored in the memory 26 to check whether the mechanical properties of the steel plate 1 are acceptable or not.

Instead of the chemical composition determined by the ladle analysis, the values determined by an on-line analyzer, such as an emission spectroscopic analyzer, provided in the inspection line may be used.

Also, the mechanical properties of steel may be evaluated on the basis of rolling conditions involving heat treatment and working instead of the chemical composition used in the example described in the foregoing. The method and apparatus according to this invention are also applicable to other mechanical properties than those described in this specification.

What is claimed is:

1. An apparatus for evaluating the mechanical properties of steel which comprises:
   a hardness measuring apparatus, grain size measuring apparatus, and emission spectroscopic analyzer provided at the terminal end of a steel rolling line; and
   a computer, the computer comprising;
   an input section into which signals from the hardness measuring apparatus, grain size measuring apparatus and spectroscopic analyzer are inputted;
   a memory in which empirical equations showing a relationship between each of tensile strength, yield point, elongation, shelf energy, transition temperature, and temperature range of an energy transition region for first steel samples and the hardness, grain size and chemical composition of the first steel samples and an energy transition curve plotting shelf energy, transition temperature, and temperature range of an energy transition region of the first steel samples are stored;
   an arithmetic logic unit that derives tensile strength, yield point, elongation, shelf energy, transition temperature, and temperature range of an energy transition region from the empirical equations stored in the memory and drives an energy absorbed at a given temperature from the energy transition curve stored in the memory using signals supplied from said measuring apparatuses and said spectroscopic analyzer when measuring hardness, grain size and chemical composition of a second steel sample; and
   a display unit showing the results of the operation carried out by the arithmetic logic unit.

2. An apparatus according to claim 1, which comprises an arithmetic logic unit that judges acceptability of the mechanical properties of the second steel sample by comparing the derived tensile strength, yield point, elongation and absorbed energy of the second steel sample with preset target values thereof.

3. A method of evaluating mechanical properties of steel which comprises the steps of:
   measuring tensile strength, yield point, elongation, hardness, grain size and chemical composition of first steel samples to be evaluated;
   determining, on the basis of the measurements thus obtained, an empirical equation for each of the tensile strength, yield point and elongation of the first steel samples in which the hardness, grain size and chemical composition thereof are contained as variables;
   measuring hardness, grain size and chemical composition of a second steel sample to be evaluated; and
   deriving the tensile strength, yield point and elongation of the second steel sample to be evaluated by substituting the hardness, grain size and chemical composition measured for the second steel sample in each empirical equation.

4. The method of evaluating mechanical properties of steel specified in claim 3 characterized by the fact that a differential hardness $$H_T = K_1 \frac{1}{D} \cdot \frac{dW}{dX};$$

$k_1$ is a constant defined from a differential of a linear segment of a load-displacement curve obtained by continuously measuring a load W with which an indenter having a diameter D is forced into the steel samples and a depth X of a resulting depression is used as hardness and an effective grain size determined by measuring attenuation of ultrasonic waves applied to the steel samples is used as grain size.

5. A method of evaluating mechanical properties of steel which comprises the steps of:
   measuring shelf energy, transition temperature, temperature range of an energy transition region, hardness, grain size and chemical composition of first steel samples;
   determining, on the basis of the measurements thus obtained, an empirical equation for each of shelf energy, transition temperature, and temperature range of an energy transition region of the first steel samples in which the hardness, grain size and chemical composition thereof are contained as variables;
   measuring the hardness, grain size and chemical composition of a second steel sample to be evaluated;
   deriving shelf energy, transition temperature, and temperature range of an energy transition region of the second steel sample to be evaluated by substituting the hardness, grain size and chemical composition measured for the second steel sample in each empirical equation; and
   determining energy absorbed at a given temperature from an energy transition curve approximated on the basis of the shelf energy, transition temperature, and temperature range of the energy transition region of the second steel sample to be evaluated using an equation $$vE_T = \begin{cases} 0 & T < T_1 \\ vEs\left(\dfrac{T - vTr_E}{T_2 - T_1} + \dfrac{1}{2}\right) & T_1 \leq T \leq T_2 \\ vEs & T_2 < T \end{cases}$$

where
vET: energy absorbed at temperature T
vEs: shelf energy
vTrE: transition temperature
$T_2 - T_1$: temperature range of the energy transition range.

6. The method of evaluating mechanical properties of steel specified in claim 5 characterized by the fact that a differential hardness $$H_T = K_1 \frac{1}{D} \cdot \frac{dW}{dX};$$

$k_1$ is a constant defined from a differential of a linear segment of a load-displacement curve obtained by continuously measuring a load W with which an indenter having a diameter D is forced into the steel samples and a depth X of a resulting depression is used as hardness and an effective grain size determined by measuring attenuation of ultrasonic waves applied to the steel samples is used as grain size.

7. A method of evaluating mechanical properties of steel which comprises the steps of:

measuring tensile strength, yield point, elongation, shelf energy, transition temperature, temperature range of an energy transition region, hardness, grain size and chemical composition of first steel samples to be evaluated;

determining, on the basis of the measurements thus obtained, an empirical equation for each of the tensile strength, yield point, elongation, shelf energy, transition temperature, and temperature range of the energy transition region of the first steel samples in which the hardness, grain size and chemical composition thereof are contained as variables;

measuring hardness, grain size and chemical composition of a second steel sample to be evaluated;

deriving the tensile strength, yield point, elongation, shelf energy, transition temperature, and temperature range of the energy transition region of the second steel sample to be evaluated by substituting the hardness, grain size and chemical composition measured for the second steel sample in said empirical equations; and determining the energy absorbed at a given temperature from the shelf energy, transition temperature, and temperature range of the energy transition region of the second steel sample to be evaluated.

8. The method of evaluating mechanical properties of steel specified in claim 7 characterized by the fact that a differential hardness $$H_T = K_1 \frac{1}{D} \cdot \frac{dW}{dX};$$

$k_1$ is a constant defined from a differential of a linear segment of a load-displacement curve obtained by continuously measuring a load W with which an indenter having a diameter D is forced into the steel samples and a depth X of a resulting depression is used as hardness and an effective grain size determined by measuring attenuation of ultrasonic waves applied to the steel samples is used as grain size.

* * * * *